(12) United States Patent
Vallittu

(10) Patent No.: US 9,084,844 B2
(45) Date of Patent: Jul. 21, 2015

(54) IMPLANT

(71) Applicant: SKULLE IMPLANTS OY, Turku (FI)

(72) Inventor: Pekka Vallittu, Kuusisto (FI)

(73) Assignee: Skulle Implants Oy, Turku (FI)

( * ) Notice: Subject to any disclaimer, the term of this patent is extended or adjusted under 35 U.S.C. 154(b) by 0 days.

(21) Appl. No.: 14/380,692

(22) PCT Filed: May 28, 2013

(86) PCT No.: PCT/EP2013/060980
§ 371 (c)(1),
(2) Date: Aug. 22, 2014

(87) PCT Pub. No.: WO2013/178637
PCT Pub. Date: Dec. 5, 2013

(65) Prior Publication Data
US 2015/0032224 A1 Jan. 29, 2015

(30) Foreign Application Priority Data

May 30, 2012 (EP) .................... 12169943

(51) Int. Cl.
| *A61F 2/02* | (2006.01) |
| *A61K 9/00* | (2006.01) |
| *A61K 33/42* | (2006.01) |
| *A61L 31/12* | (2006.01) |
| *A61L 27/44* | (2006.01) |
| *A61F 2/08* | (2006.01) |
| *A61F 2/28* | (2006.01) |
| *A61L 31/02* | (2006.01) |
| *A61L 31/16* | (2006.01) |

(52) U.S. Cl.
CPC .............. *A61L 31/125* (2013.01); *A61F 2/08* (2013.01); *A61F 2/28* (2013.01); *A61L 27/446* (2013.01); *A61L 31/026* (2013.01); *A61L 31/16* (2013.01); *A61L 2300/102* (2013.01); *A61L 2430/02* (2013.01)

(58) Field of Classification Search
CPC ......... A61L 31/16; A61L 27/10; A61L 27/12; A61L 2300/60; A61L 2300/608; A61L 31/026; A61K 9/0024
USPC .................................. 623/23.72, 1.42, 11.11
See application file for complete search history.

(56) References Cited

U.S. PATENT DOCUMENTS

| 5,626,861 A | * | 5/1997 | Laurencin et al. ............ 424/426 |
| 2006/0293760 A1 | * | 12/2006 | DeDeyne ................... 623/23.76 |
| 2010/0189764 A1 | * | 7/2010 | Thomas et al. ............... 424/426 |

FOREIGN PATENT DOCUMENTS

| JP | 2008/013672 | | 1/2008 |
| WO | WO 2004/049904 | | 6/2004 |
| WO | WO 2010/096487 | | 8/2010 |
| WO | WO 2011073507 A1 | * | 6/2011 |

* cited by examiner

Primary Examiner — Frederick Krass
Assistant Examiner — Tracy Liu
(74) Attorney, Agent, or Firm — James C. Lydon

(57) ABSTRACT

The present invention relates to an implant comprising at least two layers made of fibers and bioactive material arranged between said at least two layers, the bioactive material being selected from the group consisting of bioactive glass, hydroxyapatite, tricalciumphosphate and mixtures thereof. In the implant, at least one of the layers is at least mainly formed of a mesh, which is made of glass fibers having a diameter of 3-100 μm, and wherein the mesh size is selected such that the bioactive material is retained within the implant. In addition, the layers are embedded in a matrix made of a resin selected from the group consisting of polyesters, epoxies, acrylates and mixtures thereof, and the layers are attached to each other along the contour of the implant.

7 Claims, 5 Drawing Sheets

US 9,084,844 B2

IMPLANT

FIELD OF THE INVENTION

The invention relates to an implant comprising at least two layers made of fibers and at least one layer of bioactive material arranged between said at least two layers.

BACKGROUND

The use of reinforced composites made of particulate fillers or reinforcing fibers is already known. The state-of-the-art fiber reinforced composites yield high strength properties and by selecting the multiphase resin matrix for the composite, the handling characteristics of the composite can be considerably improved.

On the other hand, a lot of development has occurred with bioactive materials, namely bioactive ceramics and glass and sol-gel processed silica. These materials can be used to achieve attachment of e.g. bone to a biomaterial surface after the material has been put in contact with tissue. An additional advantage of bioactive glass is its antimicrobial effect on the microbes existing for instance in infected sinuses of a bone. Document WO 2004/049904 discloses bioactive, resorbable scaffolds for tissue engineering. The scaffolds are made of bioactive glass meshes that comprise interwoven bioactive glass fibers and may comprise incubating cells such as fibroblasts and chondroblasts.

From a surgical perspective, individual replacement of bone, cartilage and soft tissues are insufficient in tumour, traumatologic and tissue reconstruction surgery despite the increasing advances in biomaterials research and their clinical application methods and tissue engineering. The need and indications for development of new kinds of materials result from disadvantages of the use of allografts. Risks for transmittable diseases (HIV, Creutzfeld-Jacob's disease, etc.) are related to allografting. Metals are not bioactive or osteoconductive, and their use results in stress shielding phenomena and bone atrophy of the adjacent bone. Metal implants cause also severe problems in magnetic resonance imaging (MRI) when diagnosing diseases of patients. These main disadvantages are well documented in large clinical series.

There thus still exists a need for alternative implants for medical uses.

OBJECTS AND SUMMARY OF THE INVENTION

An object of the present invention is to provide a biologically compatible material that does not have the above-listed drawbacks, or at least those disadvantages are minimised. Specifically, an object of the present invention is to provide a material useful for medical, dental and surgical uses, such as for bone grafting in repair of bone defects and fixation of fractured pieces of bone.

DETAILED DESCRIPTION OF THE INVENTION

Figure 1:
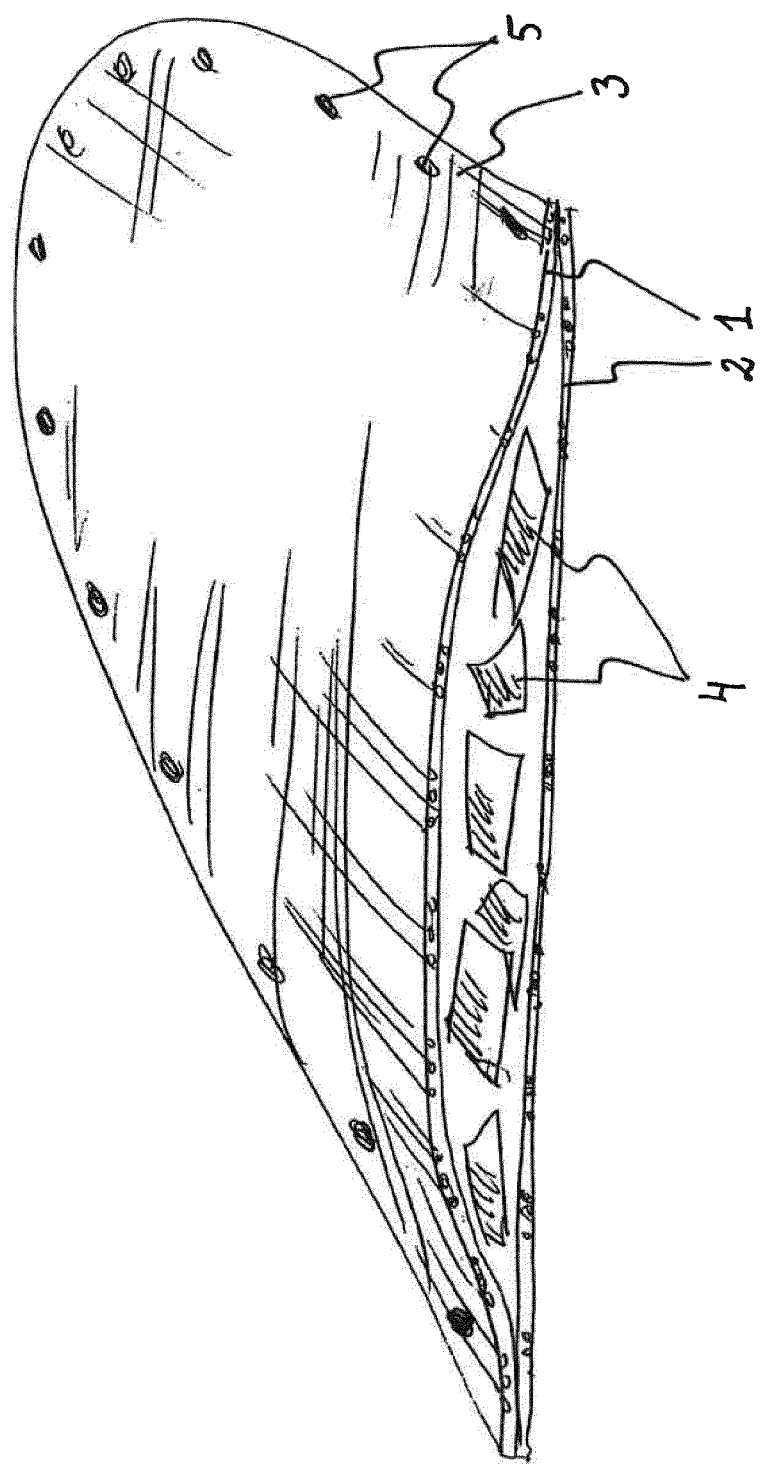
FIG. 1 schematically shows an implant according to a first embodiment.

The invention relates to an implant comprising at least two layers made of fibers and at least one layer of bioactive material arranged between said at least two layers.

A typical implant according to this invention comprises at least two layers made of fibers and bioactive material arranged between said at least two layers. A least one of the layers is at least mainly formed of a mesh made of glass fibers having a diameter of 3-100 µm, and the mesh size is selected such that the bioactive material is retained within the implant. Moreover, the layers are embedded in a matrix made of a resin selected from the group consisting of polyesters, epoxies, acrylates and mixtures thereof, and the layers are attached to each other along the contour of the implant. Furthermore, the bioactive material is selected from the group consisting of bioactive glass, hydroxyapatite, tricalciumphosphate and mixtures thereof The implant according to this invention thus takes advantage of the capillary effect, as at least one of the surfaces is formed at least mainly of a mesh. Indeed, the structure of the implant, due to the use of at least one mesh and a bioactive material, is such that the capillary effect is enhanced, thus leading to improved bone ingrowth, as fluids can penetrate inside of the implant better than if both surfaces were made of a tightly woven cloth or a film. In addition, the openings of the mesh allow the penetration of the body fluids to occur from various directions of the implant which means that the fluid penetration is not sensitive to the direction of blood flow from arteries.

The implant may have both its outer surfaces made of a mesh or one of the surfaces may be made of a film or a tightly woven cloth. When the other surface is not made of a mesh, it is typically the surface that will be on the outside once the implant is in its place. The implant may also comprise more than two layers, such as three, four or five layers. According to an embodiment, the layer thickness is about 500-700 µm. The thickness of the implant depends for example on the thickness of the bone it intends to replace. Most typically, a maximum thickness of 10 mm is achieved with five layers. When several layers are used, the intermediate (i.e. the inner layers as opposed to the outermost layers) are preferably made of mesh. According to a preferred embodiment, all the layers are impregnated with a resin, i.e. embedded in a matrix. The resin chosen may be the same or different for each layer. Furthermore, when several layers are used, only the two outermost may be attached to each other along the contour of the implant or all or some of the other layers (intermediate layers) may be attached to each other in a similar manner.

In this specification, by curing it is meant polymerisation and/or crosslinking. By matrix, it is understood the continuous phase of a composition and by uncured matrix it is meant a matrix that is in its deformable state but that can be cured, i.e. hardened, to an essentially non-deformable state. The uncured matrix may already comprise some long chains but it is essentially not yet polymerised and/or crosslinked. By prepreg, it is meant a semi-manufactured product, that is, a product that is not or only partly polymerised, but yet still deformable. The curing of a resin leads to a composite material, wherein the cured resin forms the matrix.

The layers of the implant are at least mainly formed of a mesh, meaning that at least 55% of the surface of the layer is made of mesh. Preferably, at least 60, 65, 70, 75, 80, 85, 90 or 95% of the surface is made of mesh. As will be explained later, the layers may also comprise zones where the layer is in another form than mesh, such as tightly woven cloth or continuous fibers. Typically these zones are used for cutting or bending the implant. Most preferably the layers are made of a mesh except for these zones. Sometimes the contour of the layers may be made of continuous fibers. This may be used for example in implant where they are attached to the bone in an area where the bone (and thus the attachment) is under significant stress. Therefore, the continuous fibers reinforce the contour where attachment to the bone takes place.

According to one embodiment of the invention, the fibers are selected from the group consisting of inert glass fibers and bioactive glass fibers. According to another embodiment, the glass fibers are made of a glass composition of E-glass, S-glass, R-glass, C-glass or bioactive glasses.

According to yet another embodiment, the diameter of the fibers is 4-25 μm. The diameter of the fibers can be for example from 3, 5, 6, 10, 15, 20, 25, 30, 40, 45, 50, 60, 70 or 80 μm up to 5, 6, 10, 15, 20, 25, 30, 40, 45, 50, 60, 70, 80, 90 or 100 μm. Fibers in the nanometer scale, i.e. with a cross-sectional diameter varying between 200-1000 nm can also be used.

The bioactive material can be in any form suitable for inserting between two layers consisting mainly of a mesh. It may be for example in the form of a monolith or in particle form. By particles, it is meant entities wherein the largest dimension is no more than five times larger than the smallest dimension. It may thus also be in the form of chopped, short fibers. When particles are used, their size is smaller than the mesh size of the layers, in order for the layer to be able to retain them inside the implant. The bioactive material may also be in the form of a monolith or just two, three or four large particles. Some possible particles sizes are 10-1000 μm. The particle size can be for example from 10, 20, 50, 100, 150, 200, 250, 300, 400, 500, 650, 700 or 800 μm up to 20, 50, 100, 150, 200, 250, 300, 400, 500, 650, 700, 800, 900 or 1000 μm.

The bioactive material may also be in the form of a fluid having a viscosity such that the layers of mesh are impermeable to the fluid, that is, the implant may comprise such bioactive material in addition to those listed in the independent claim. The fluid can be a highly viscous fluid or a colloid in fluid form. By colloid, it is meant a substance microscopically dispersed evenly throughout another substance. The bioactive material may naturally also be in several of these forms, for example a combination of particles in a fluid. Preferably, the bioactive material is bioactive glass.

According to an embodiment, mesh size is optimized by weaving process of the mesh and viscosity and amount of impregnation resin of the mesh. According to an embodiment, the mesh size is preferably 1 to 5 micrometers less than the smallest diameter of the particles. The mesh size may be for example 9-999 μm. The mesh size may thus be for example from 1, 2, 3, 5, 7, 9, 10, 15, 20, 50, 100, 150, 200, 250, 300, 400, 500, 650, 700, 800 or 900 μm up to 2, 3, 5, 7, 9, 10, 15, 20, 50, 100, 150, 200, 250, 300, 400, 500, 650, 700, 800, 900, 950 or 1000 μm.

According to a further embodiment, the two layers of mesh are attached to each other also along at least one cutting line. The cutting line may be formed for example of unidirectional continuous fibers.

The attachment zone, i.e. the part of the implant where the layers are attached together, can be varied in width. The advantage of a large attachment zone is that the implant can be cut smaller to fit to the intended use, yet it still remains functional as the bioactive material is retained within the implant.

The positioning of the attachment zone is also important and can be varied depending on the intended use. For example, the implant may be made such that it has more than one part (for example two, three, four, five or six parts), each part being separated from the other parts by an attachment zone, i.e. a cutting line. The attachment zones between the parts can be used for example for easier bending of the implant or for cutting one or more parts out from the implant. Thus a versatile implant can be made whereby the user will have to decide what size it needed only just before implanting the implant. This is especially important for emergency operations and is also believed to reduce costs as it will no longer be necessary to keep a stock of different sizes of implants. The shelf-life of these implants is believed to be approximately one year, depending naturally of the components used.

The contour of the implant, i.e. the attachment zone along the contour may also contain holes that extend through both layers of the mesh to ease the attaching of the implant to place with for example bone screws. Similar holes may be also provided in a cutting line if needed. Moreover, when a large attachment zone along the contour of the implant is used, it may be equipped with a series of holes at different distances from the edges such that the implant is still easily attachable even when cut to a smaller size.

The implant may be homogenous in its structure and materials or it may consist of different materials and/or properties at different locations. It is for example possible to vary one or more of the following: the mesh size, the matrix material, the amount of matrix, the fiber material, the fiber diameter or the bioactive material. This could lead to for example different strengths at different locations of the implant.

A preferred matrix material is an acrylate polymer. The matrix is formed when the resin is cured. According to an embodiment, the matrix resin is selected from the group consisting of substituted and unsubstituted dimethacrylates and methacrylates. Some especially advantageous matrix materials (monomers) are methyl acrylate, methyl methacrylate, methacrylate functionalized dendrimers, glycidyl dimethacrylate (bis-GMA), triethylene glycol dimethacrylate (TEGDMA) and urethane dimethacrylate (UDMA). The materials may be used as blends and they may form interpenetrating polymer networks (IPNs). They may also be functionalised with bioactive molecules that allow for a drug-like contact effect. Combinations of monomers and polymers are also suitable to be used, including modifications of resin systems by antimicrobial side group containing iodine which offers additional benefit in increasing radio opacity of the resin system.

The viscosity of the resin is such that it does not obstruct the mesh structure. Some examples of resin viscosity and mesh size are given below.

The implant may further comprise modifier particles. These modifier particles may for example be bioactive and for example improve the osteoconductivity of the implant. The particles may be in the form of particulate fillers or fibers. The weight fraction of these modifier particles in the implant can be for example 10-60 wt-%, such as from 5, 10, 15, 20, 35 or 50 wt-% up to 10, 15, 20, 35, 50, 55, 60 or 75 wt-%.

According to one embodiment, the modifier particles are selected from the group consisting of bioactive ceramics, bioactive glass, silica gel, titanium gel, silica xerogel, silica aerogel, natrium silica glass, titanium gels, bioactive glass ionomer, hydroxyapatite, Ca/P-doped silica gel and mixtures thereof. Any combination of said materials may naturally also be used. When rapid mineralization is needed, it is preferred to have bioactive glass with sol-gel processed silica particles.

The implant according to the present invention may further comprise additional particulate filler material, such as metal oxides, ceramics, polymers and mixtures thereof. Metal oxides may for example be used as radio or X-ray opaque materials or as colouring materials.

The implant may also comprise therapeutically active agents or cells such as stem cells, proteins such as growth factors and/or signalling molecules. Several kinds of cells including hematopoietic bone marrow cells, fibroblasts, osteoblasts, regenerative cells, stem cells, like embryonic stem cells, mesenchymal stem cells or adipose stem cells can be seeded to the implant. The embryonic stem cells may or may not be of a human origin. Stem cells seeded to the implant can be cultured in bioreactors ex vivo, in other parts of the body before inserting the formed tissue into its final place, or directly at the place where regenerative and reconstructive treatment is needed. The implant may contain also additives enhancing its processability, such as polymerisation initiators. The materials of the implant can be either bioresorpable, biodegradable, biostable or a mixture of these.

The implant may also contain, between the layers, interconnective parts that are rigid and essentially non-compressible. These interconnective parts thus ensure that when the material is bent, the layers do not come into contact with each other, as they should remain spaced apart. This then ensures that the properties of the implant remain essentially intact with respect to the capillary effect and bone ingrowth.

The size and shape of the implant is selected according to the intended use. The diameter of the implant can be for example from 10 to 350 mm. The shape can be any suitable shape such as circular, elliptic, square etc. The implant may also have a cross-section that is essentially symmetrical with respect to the two layers, i.e. they are equally spaced apart along essentially the whole width of the implant. The implant may also have different shapes as will be explained in more detail in connection with the drawing. The implant may thus have an essentially flat upper (or lower) surface and an extension on the other surface. Such forms are especially suitable for cranial uses for filling in bur holes after surgery.

The implant may be used for reconstitution of bones following a trauma, a defect or a surgery of diseases. Implant reconstruction of damaged or missing parts of skeleton is performed by providing immediate repair of an anatomical shape and adequate mechanical support of the remaining pieces of bone with simultaneous penetration of blood and bone forming cells from the adjacent tissues to the implant. Typically the needs are in repairs of calvarial bone defects after neurosurgical operations and traumas, in reconstructions of bony orbital floors and jaw bones, but the implant can be used also in orthopaedics and spine surgery as well as in fixation of fragmented pieces of bone. In the presence of long bones weakened by diseases, or when parts of the cortical bone are lost, the implant can be used to reinforce the long bones and cover openings where cortical bone is lost. In tissue engineering applications, the implant fabricated to the desired form can be loaded with stem cells and the tissue formed in bioreactor or in adjacent tissues of the patient before application of the implant to the final location.

The implant is preferably manufactured as follows. A two-piece mould is produced from translucent mould material to give the shape for the implant's both sides. Typically, the implant's outer surface is made thicker and not mesh-like whereas the inner surface which is going to be in contact with the blood circulation of the damaged tissues, is made mesh-like. In the cases where better permeability of the implant by fluids and/or tissue is preferred, the outer surface is also made of mech-like material. Fiber fabric for the outer surface is typically fully impregnated with the monomer resin system and the fiber fabric is placed to the mold. Particles of bioactive glass are poured on the inner surface of the outer surface layer thus formed. To produce the mesh-like inner surface for the implant, a mesh-like fibre fabric is impregnated with monomer resin. By varying the amount of monomer resin and its viscosity in the fibre fabric, sizes of the openings in the inner laminate can be varied. Some examples of suitable viscosities are as follows. The viscosity of the monomer resin glycidyl dimethacrylate and triethylene glycol dimethacrylate may vary from 550 Pa·s of pure glycidyl dimethacrylate to 50 Pa·s of triethylene glycol dimethacrylate. Mixture of 50%:50% of glycidyl dimethacrylate and triethylene glycol dimethacrylate may have a viscosity of 180 Pa·s and the resin can be used to impregnate a fiber mesh having size of the openings to be 300 micrometers. By increasing the proportion of glycidyl dimethacrylate, the viscosity of the mixture increases and larger openings of the fiber mesh can be used to have the final mesh (opening) size of 300 micrometers. The viscosities are given for a temperature of 25° C.

The mesh-like fabric is placed on top of the implant's outer layer laminate and bioactive particles, followed by closing the mould system. Through the translucent mould material, the initial polymerization of the monomer resin system is initiated with light. A photosensitive initiator and activator system in the monomer resin of the implant will initially become polymerised. The mould is opened and the initially polymerised implant is released from the mould and the curing is completed in vacuum and at elevated temperature before finishing the implant (rounding the contours etc).

Some embodiments of the invention are explained in more detail in the enclosed drawing, which is not to be construed as limiting the claims. The reference signs are also not to be construed as limiting the claims.

DETAILED DESCRIPTION OF THE DRAWING

In the following, the same reference signs are used of the same or similar components in different embodiments and/or Figures.

FIG. 1 schematically shows an implant according to a first embodiment. In this embodiment, the implant consists of two layers, a first upper layer 1 and a second lower layer 2 made of a fiber mesh. The layers are attached to each other along the contour 3 of the implant and bioactive particles 4 are arranged between the layers. The contour 3 also contains holes 5 that extend through both layers 1 and 2 to ease the attaching of the implant to place with for example bone screws.

Figure 2:
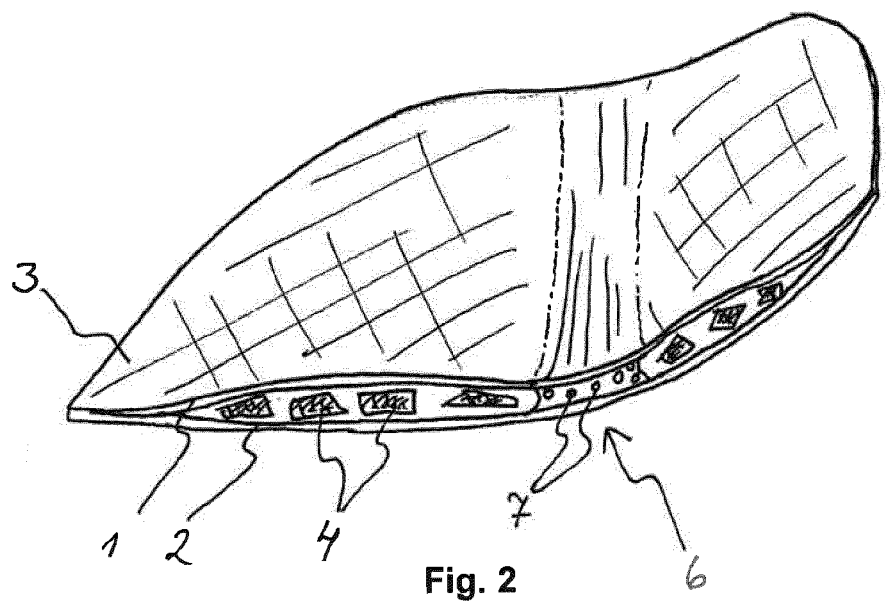
FIG. 2 schematically shows an implant according to a second embodiment.
Figure 3:
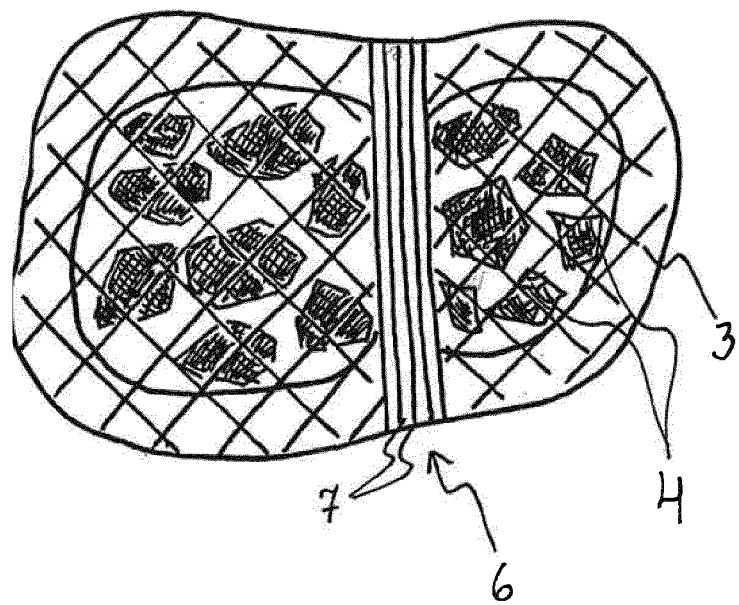
FIG. 3 schematically shows the implant according to the second embodiment, from a different angle.

FIG. 2 schematically shows an implant according to a second embodiment. In this embodiment, the implant is an orbital plate consisting of two layers, a first upper layer 1 and a second lower layer 2 made mainly of open hole woven fiber reinforced composite mesh. The layers also have a cutting line 6 made of unidirectional long fibers 7. The layers are attached to each other along the contour 3 of the implant as well as along the cutting line 6. Bioactive particles 4 are arranged between the layers. FIG. 3 schematically shows the implant according to the second embodiment, from a different angle, i.e. perpendicularly to the layers. In this Figure, it can be seen that the cutting line 6 consists of continuous unidirectional fibers 7 extending from one end of the implant to the other. This Figure also shows how the mesh size of the layers is smaller than the size of the particle 4. The Figure also shows the width of the attachment zone along the contour 3.

Figure 4:
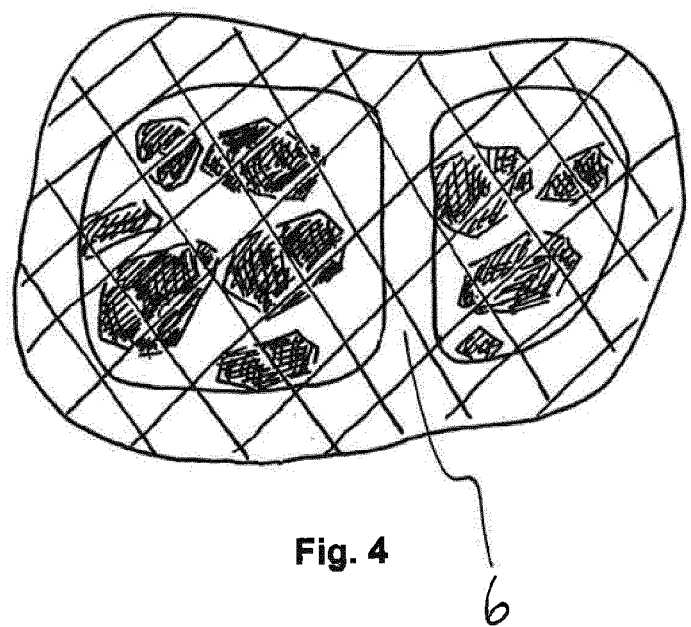
FIG. 4 schematically shows an implant according to a third embodiment.

FIG. 4 schematically shows an implant according to a third embodiment. In this embodiment, the cutting line 6 is made of the same material as the rest of the layers and formed by simply attaching the layers to each other.

Figure 5:
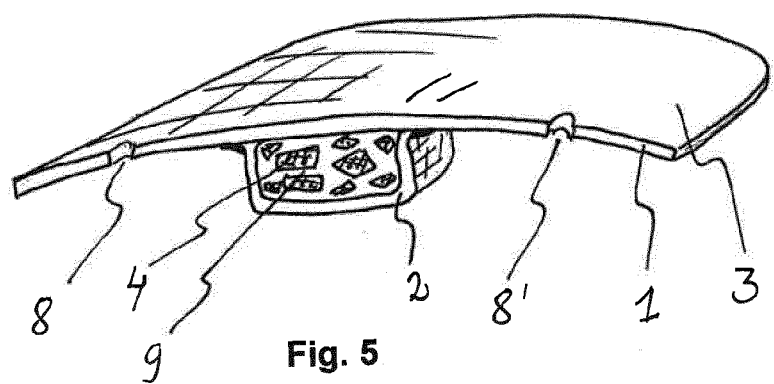
FIG. 5 schematically shows an implant according to a fourth embodiment.

FIG. 5 schematically shows an implant according to a fourth embodiment. In this embodiment, the implant is a fixation stub for bone flaps following a craniotomy. The attachment zone 3 is quite large in this embodiment, in order to allow for good adhesion of the implant to the bone. The attachment zone 3 also has two holes 8, 8' for fixation screws, shown as half holes in this Figure. The first, upper layer 1 is in this embodiment essentially flat and the second, lower layer 2 forms an extension 9 under the first layer 1. The size and shape of the extension 9 is essentially identical to the bur holes in the calvarial bone. These extensions also contain bioactive particles 4 to enhance bone ingrowth.

Figure 6:
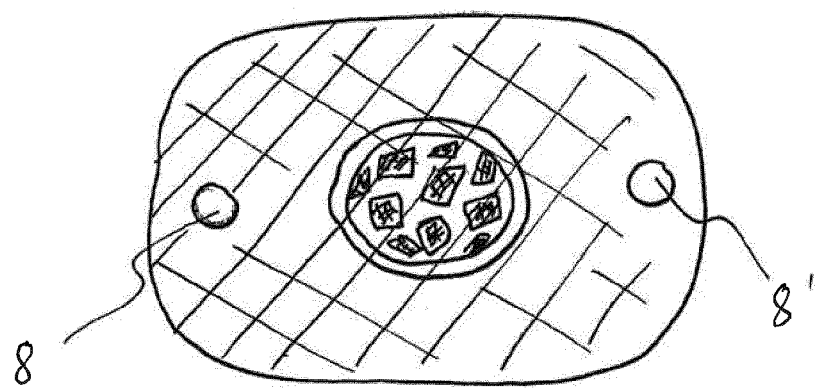
FIG. 6 schematically shows the implant according to the fourth embodiment, from a different angle.

FIG. 6 schematically shows the implant according to the fourth embodiment, from a different angle and the two holes 8, 8' for fixation screws can be seen clearly.

Figure 7:
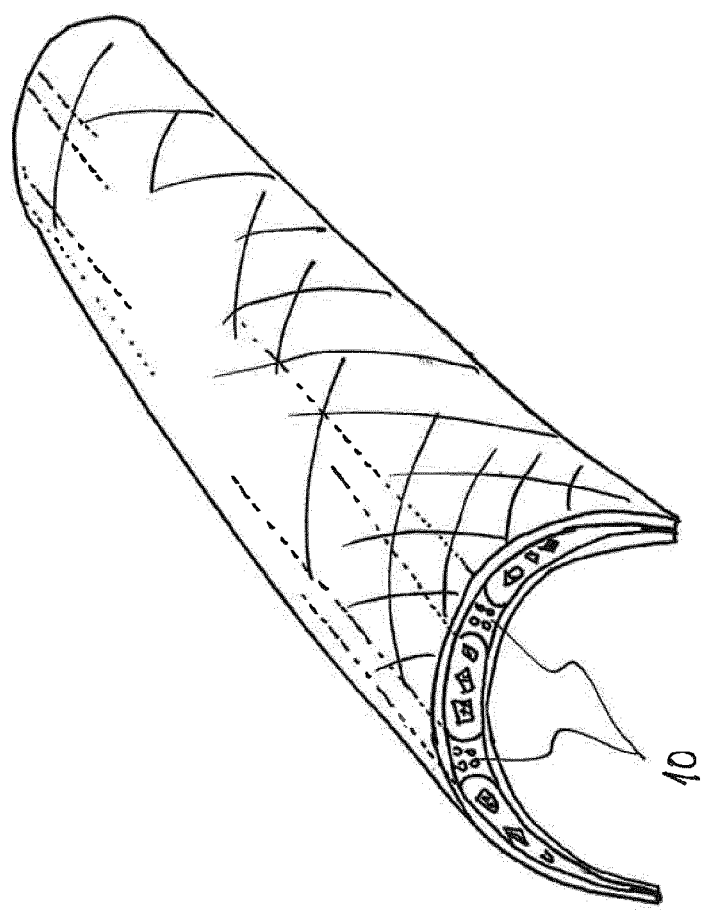
FIG. 7 schematically shows an implant according to a fifth embodiment.

FIG. 7 schematically shows an implant according to a fifth embodiment. In this embodiment, the implant is a covering plate for bone defects of long bones. The implant contains also interconnective parts 10 ensuring that when the material is bent, the layers do not come into contact with each other in areas where they should remain spaced apart in order for allowing good bone ingrowth.

The invention claimed is:

1. An implant comprising at least two layers made of fibers and bioactive material arranged between said at least two layers, wherein
at least one of the layers comprises a mesh
made of glass fibers having a diameter of 3-100 µm, and wherein
the mesh size is selected such that the bioactive material is retained within the implant,
the layers are embedded in a matrix made of a resin selected from the group consisting of substituted and unsubstituted dimethacrylates and methacrylates,
the layers are attached to each other along the contour of the implant, and
wherein the bioactive material is in particle form and is selected from the group consisting of bioactive glass, hydroxyapatite, tricalciumphosphate and mixtures thereof.

2. An implant according to claim 1, wherein the glass fibers are made of a glass composition of S-glass, E-glass or bioactive glass.

3. An implant according to claim 1, wherein the diameter of the fibers is 4-25 µm.

4. An implant according to claim 1, wherein the particle size of the bioactive material is 10-1000 µm.

5. An implant according to claim 1, wherein the mesh size is 9-990 µm.

6. An implant according to claim 1, wherein the two layers of mesh are further attached to each other along at least one cutting line.

7. An implant according to claim 6, wherein the cutting line is formed of unidirectional continuous fibers.

\* \* \* \* \*